(12) United States Patent
Skibbe et al.

(10) Patent No.: US 12,178,173 B2
(45) Date of Patent: Dec. 31, 2024

(54) INCREASING PLANT TRANSFORMABILITY BY CYTOTYPE TRANSFER

(71) Applicant: SYNGENTA CROP PROTECTION AG, Basel (CH)

(72) Inventors: David Stewart Skibbe, Research Triangle Park, NC (US); Sivamani Elumalai, RTP, NC (US)

(73) Assignee: Syngenta Crop Protection AG, Basel (CH)

( * ) Notice: Subject to any disclaimer, the term of this patent is extended or adjusted under 35 U.S.C. 154(b) by 44 days.

(21) Appl. No.: 17/600,734

(22) PCT Filed: Mar. 24, 2020

(86) PCT No.: PCT/US2020/024440
§ 371 (c)(1),
(2) Date: Oct. 1, 2021

(87) PCT Pub. No.: WO2020/205334
PCT Pub. Date: Oct. 8, 2020

(65) Prior Publication Data
US 2022/0174901 A1    Jun. 9, 2022

Related U.S. Application Data

(60) Provisional application No. 62/827,450, filed on Apr. 1, 2019.

(51) Int. Cl.
| | | |
|---|---|---|
| A01H 6/46 | (2018.01) | |
| A01H 1/04 | (2006.01) | |
| C12N 15/82 | (2006.01) | |

(52) U.S. Cl.
CPC ........... *A01H 1/045* (2021.01); *A01H 6/4684* (2018.05)

(58) Field of Classification Search
None
See application file for complete search history.

(56) References Cited

U.S. PATENT DOCUMENTS

| | | | |
|---|---|---|---|
| 6,096,947 A | 8/2000 | Jayne et al. | |
| 6,346,612 B1 | 2/2002 | Fauron et al. | |
| 2004/0016030 A1* | 1/2004 | Lowe ................. | C12N 15/8205 800/294 |
| 2008/0072343 A1 | 3/2008 | Wang et al. | |
| 2008/0078003 A1 | 3/2008 | Zuo-Yu et al. | |
| 2018/0332790 A1 | 11/2018 | Kelliher et al. | |

FOREIGN PATENT DOCUMENTS

| | | |
|---|---|---|
| WO | 2000061812 A1 | 10/2000 |
| WO | 2010027948 A2 | 3/2010 |
| WO | 2016102665 A2 | 6/2016 |
| WO | 2018102816 A1 | 6/2018 |

OTHER PUBLICATIONS

Allen et al., "Comparisions Among Two Fertile and Three Male-Sterile Mitocjondrial Genomes of Maize." Genetics Society of Americ, Oct. 1, 2007, vol. 177, No. 2, pp. 1173-1192.
Bosacchi et al., "Plastid Genotyping Reveals the Uniformity of Cytoplasmic Male Sterile-1 Maize Cytoplasms," Plant Physiology, Sep. 2, 2015, vol. 169, No. 3, pp. 2129-2137.
International Search Report Cited in International Application No. PCT/US2020/024440, Mailed Jul. 1, 2020.
Allen, James O., "Effect of Tesointe Cytoplasmic Genomes on Maize Phenotype", Genectics Society of America, Feb. 2005, vol. 169, pp. 863-880.
Chase, Sherret S., "Androgenesis—It's Use for Transfer of Maize Cytoplasm", Journal of Heredity, vol. 54, Issue 4, Jul. 1963, pp. 152-158.
Chen, Letian, et al., "Male Sterility and Fertility Restoration in Crops", Annual Review of Plant Biology, 2014, vol. 64, pp. 579-606.
Fauron, Cristiane et al., "The Maize Mitochondrial Genome of The Normal Type and The Cytoplasmic Male Sterile Type T Have Very Different Organization", Current Genetics, 1989, vol. 15, pp. 149-154.
Fauron, Christiane et al., "The Maize Mitochondrial Genome: Dynamic, Yet Functional", TIG, Jun. 1995, vol. 11, No. 6, pp. 228-235.
Fauron, Christiane M.R., "A Second Type of National Maize Mitochondrial Genome: An Evolutionary Link", Genetics, vol. 137, pp. 875-882, Jul. 1994.
Gabay-Laughnan, S. et al., "Mitochondrial Mutations in Maize", Maydica, vol. 50, 2005, pp. 349-359.
Green, C.E. et al., "Plant Regeneration from Tissue Cultures of Maize", Crop Science, CVol. 15, May-Jun. 1975, pp. 417-421.
Sanagare, Abdourhamane, e al., "Localization and Organization of tRNA Genes on the Mitochondrial Genomes of Fertile and Make Sterile Lines of Maize", Mol. Gen. Genet., vol. 223, pp. 224-232, 1990.
Zeven, A.C., "The Origin and Survival of Polyploids in Cytotype Mixtures", Polyploidy, pp. 385-407, 1979.
Willman, M.R. et al., "Inheritance of Somatic Embryogensis and Plantlet Regeneration from Primary (Type 1) Callus in Maize", In Vitro Cellular and Developmental Biology, vol. 25, No. 1, Jan. 1989.
Leaver, et al., "Mitochondrial Genome Diversity and Cytoplasmic Male Sterility in Higher Plants", Philosophical Transactions of the Royal Society of London. Series B, Biological Sciences, vol. 319, No. 1193, Mitochondrial Biogenesis, May 31, 1988, pp. 165-176.

(Continued)

*Primary Examiner* — Medina A Ibrahim
(74) *Attorney, Agent, or Firm* — Amanda Bublitz

(57) ABSTRACT

A method of altering or transferring the cytotype of a plant line. In particular, transferring the cytotype of a transformation-recalcitrant plant line, e.g., a transformation-recalcitrant maize line, from a transformation-recalcitrant cytotype to a transformable cytotype so that the line becomes transformable while preserving its nuclear genome. The newly-transformable line may be produced using methods including backcrossing and/or haploid induction.

14 Claims, No Drawings

Specification includes a Sequence Listing.

(56) References Cited

OTHER PUBLICATIONS

Fauron, et al., "The maize mitochondrial genome: dynamic, yet functional", TIG, vol. 11, No. 6, Jun. 1995, pp. 228-293.
Fauron, et al. "A Second Type of Normal Maize Mitochondrial Genome: An Evolutionary Link", Genetics 137, pp. 875-882, Jul. 1994.

* cited by examiner

```
                            SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
atggtgccaa ttcgtaattt aagtt                                              25

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
acccctctgg ttgcctctct                                                    20

<210> SEQ ID NO 3
<211> LENGTH: 20
<212> TYPE: DNA
<213> ORGANISM: Artificial Sequence
<220> FEATURE:
<223> OTHER INFORMATION: probe

<400> SEQUENCE: 3
tatgaagaag aataccatcc                                                    20

<210> SEQ ID NO 4
<211> LENGTH: 16
<212> TYPE: DNA
<213> ORGANISM: Artificial Sequence
<220> FEATURE:
<223> OTHER INFORMATION: probe

<400> SEQUENCE: 4 aatccctcc agtttc                                                         16

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
gtattcgcac ctactctgcc g                                                  21

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
aaagcaaaaa taccattgca acc                                                23
```

```
<210> SEQ ID NO 7
<211> LENGTH: 19
<212> TYPE: DNA
<213> ORGANISM: Artificial Sequence
<220> FEATURE:
<223> OTHER INFORMATION: probe

<400> SEQUENCE: 7
cgtaaatttt gtttgatgc                                                    19

<210> SEQ ID NO 8
<211> LENGTH: 21
<212> TYPE: DNA
<213> ORGANISM: Artificial Sequence
<220> FEATURE:
<223> OTHER INFORMATION: probe

<400> SEQUENCE: 8
atcgtaaatt tttttgatg c                                                  21
```

INCREASING PLANT TRANSFORMABILITY BY CYTOTYPE TRANSFER

RELATED APPLICATION INFORMATION

This application is a 371 of International Application No. PCT/US2020/024440, filed Mar. 24, 2020, which claims priority to U.S. Provisional Application No. 62/827,450, filed Apr. 1, 2019, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled CYTOTYPETRANSFER_ST25.txt, 1.74 kilobytes in size, generated on Sep. 30, 2021 and filed via EFS-Web is provided in lieu of a paper copy. This Sequence Listing is hereby incorporated by reference into the specification for its disclosures.

CROSS-REFERENCE TO RELATED APPLICATIONS

This application claims priority under 35 U.S.C. § 119 to U.S. Provisional Application 62/827,450, filed Apr. 1, 2019, which is incorporated herein by reference in its entirety.

SEQUENCE LISTING

This application is accompanied by a sequence listing entitled CYTOTYPETRANSFER_ST25.txt, created Mar. 16, 2020, which is approximately 2 kilobytes in size. This sequence listing is incorporated herein by reference in its entirety. This sequence listing is submitted herewith via EFS-Web and is in compliance with 37 C.F.R. § 1.824(a)(2)-(6) and (b).

FIELD OF THE INVENTION

The present invention related to the field of plant biotechnology. In particular, it relates to plant transformation, including maize transformation, and to methods of increasing a recalcitrant line's ability to accept foreign transgenes.

BACKGROUND

Plant transformation, that is, the stable integration of foreign DNA ("transgenes") into a plant genome, has been used for decades to add new and useful traits to crops. See, e.g., U.S. Pat. No. 6,051,409, filed Sep. 23, 1996, incorporated herein by reference in its entirety (disclosing maize transformation); U.S. Patent Application Publication 2008/0229447, filed Mar. 12, 2007, incorporated herein by reference (disclosing soybean transformation). One recent example includes corn even MIR604, which comprises an insecticidal protein derived from bacteria (U.S. Pat. No. 7,361,813, incorporated by reference in its entirety). But while some maize lines are relatively easy to transform (i.e., accepting of transgenic DNA), most lines are not. For example, most elite inbred lines (lines which have been selfed over several generations to obtain a pure or nearly pure homozygous genome and which are used as parent lines to create commercially valuable hybrids) cannot be transformed with foreign DNA. Thus, in order to "move" a transgenic trait into an inbred line, the transgenic trait must first be transformed into a transformable maize line. That transformed maize line is rarely suitable for use as a parent line in breeding platforms. Therefore, the transformed maize line is crossed into an inbred line to create a progeny plant which will comprise, in a heterozygous manner, the genomes of both the inbred parent and the transformed parent. Then, that progeny plant comprising the transgene must be backcrossed into the inbred line for approximately six or seven generations in order to eliminate, as much as possible, the genome contributed by the transformed parent while retaining the transgenic trait. This process generally takes two to three years. At the end of this process, one finally has obtained an inbred line comprising the transgenic trait.

Maize is not a uniform species. It exhibits extraordinary diversity, whether it is dent corn (also known as "field corn," having high starch and used for animal feed, ethanol production, or corn flour production), flint corn (also known as "Indian corn" and known by its multitude of colors), sweet corn (consumed mostly by humans, frequently as corn on the cob), or popcorn. While much of this diversity is due to the differences found between genomes of different maize lines, some of this diversity is also due to the genomes of the mitochondria—subcellular organelles that provide chemical energy for all cells—that accompany the lines. Mitochondria have their own DNA, and that mitochondrial genome is indicative of the maize cytotype. For example, maize is known to have at least five different cytotypes: normal A ("NA"), normal B ("NB"), cytoplasmic-male-sterile C ("CMS-C" or "C"), cytoplasmic-male-sterile S ("CMS-S" or "S"), and cytoplasmic-male-sterile T ("CMS-T" or "T"). Other cytotypes may still be discovered. Mitochondria, by way of their genome, may thus have an outsized effect, comparatively speaking, on the host cell's phenotype. But we are still just learning what those effects may be.

Here, we discovered for the first time that there is a relationship between transformability and cytotype. Maize lines known as being transformable have the NA cytotype, whereas known recalcitrant maize lines have the NB cytotype. Therefore, we wondered: can we change the cytotype of a recalcitrant inbred and make it transformable? If so, we could revolutionize maize transformation and greatly speed up farmers' access to new traits in commercially relevant germplasm.

SUMMARY

Provided here is a method of changing a recalcitrant plant's cytotype to make the recalcitrant plant transformable. This is accomplished by collecting pollen from the recalcitrant plant and using it to pollinate a recipient plant with a transformable cytotype. From that pollination event, a progeny embryo is obtained having the transformable cytotype (inherited from the maternal parent) while also having in its nuclear genome a set of chromosomes inherited from the recalcitrant paternal parent. This progeny embryo, whether transformed directly or induced to form callus tissue or grown into a plant, has a higher transformation efficiency than its recalcitrant parent. In some cases, the recalcitrant parent has the NB cytotype or the cytoplasmic male sterile cytotypes CMS-C, CMS-S, or CMS-T.

The recipient plant is acting as the maternal parent when it receives the pollen from the recalcitrant plant (acting as the paternal parent). The recipient plant may be a haploid inducer plant, which is to say any progeny of the recipient plant may possess only half the normal number of chromosomes. For example, the recipient plant may be a paternal haploid inducer plant, which causes some progeny to lose the maternal chromosomes (and thereby retaining only the paternal chromosomes). A paternal haploid inducer plant may comprise a mutation in an ig1 gene or a CENH3 gene. See U.S. Pat. No. 7,439,416, filed Jan. 7, 2005 (disclosing the IG1 gene) and U.S. Pat. No. 8,618,354, filed Oct. 5, 2010 (disclosing CENH3 mutations), both of which are incorporated herein by reference in their entireties. When the recipient plant is a paternal haploid inducer, the progeny resulting from the claimed method will comprise the recalcitrant plant's nuclear genome (i.e., as haploid) but the recipient plant's cytotype.

When the recipient plant is not a haploid inducer plant, progeny resulting from the claimed method will comprise the recalcitrant plant's nuclear genome and the recipient plant's nuclear genome (i.e., as normal diploid) and with the recipient plant's cytotype. In this case, backcrossing with the recalcitrant plant may be desired in order to increase the percentage and epigenetic status of the recalcitrant plant's nuclear genome relative to the presence of the recipient plant's nuclear genome in the progeny, while still retaining the desired transformable cytotype. The first progeny (F1 generation) produced by the claimed method will comprise the NA cytoplasm and a nuclear genome comprising half recipient parent genome and half recalcitrant parent genome. After one backcross ("BC") with recalcitrant parent pollen, the second generation (i.e., BC2 generation progeny) will comprise the NA cytoplasm and a nuclear genome comprising 75% from recalcitrant parent and 25% from recipient parent. Further progeny generations, e.g., BC3, BC4, etc., will have a smaller and smaller ratio of recipient nuclear genome to recalcitrant nuclear genome. Selection of the desired nuclear genotype can be accelerated through the use of molecular markers to select for the desired parent. The selection process without markers is shown in the table below:

TABLE 1

Diminishing presence of maternal genome in backcross progeny generations, using recalcitrant plant as pollen provider without selection.

| Progeny Generation | Cytotype | Percent Recipient Genome | Percent Recalcitrant Genome |
| --- | --- | --- | --- |
| F1 | NA | 50% | 50% |
| BC2 | NA | 25% | 75% |
| BC3 | NA | 12.5% | 87.5% |
| BC4 | NA | 6.25% | 93.75% |
| BC5 | NA | 3.13% | 96.88% |
| BC6 | NA | 1.56% | 98.44% |
| BC7 | NA | 0.78% | 99.22% |

By practicing the claimed method, it is possible to increase the transformation efficiency rate in a recalcitrant plant line, such that when tissue derived from the progeny plant or embryo is transformed, it will have a higher success rate than its recalcitrant line parent.

Accordingly, one embodiment of the invention is a method of increasing the success of inserting desired DNA into a maize plant cell's chromosomes, i.e., increasing transformation efficiency rate in a recalcitrant maize line, by cytotype transfer. This is done by (a) collecting pollen from a recalcitrant maize plant; (b) pollinating the silks of another maize plant which has the normal A ("NA") cytoplasm with pollen from the recalcitrant maize plant; and (c) allowing progeny embryos to form. In successful cytotype transfers, the progeny embryo has the NA cytoplasm and at least the nuclear genome of the recalcitrant maize plant (if haploid, the progeny will only have the chromosomes of the recalcitrant maize plant; if diploid, this progeny will have chromosomes from both parent plants). This progeny embryo possesses a higher transformation efficiency rate than the recalcitrant maize plant.

Another embodiment is a method of conferring transformability to a recalcitrant maize line. This is done by (a) collecting pollen from a recalcitrant maize plant; (b) pollinating the silks of another maize plant which has the normal A ("NA") cytoplasm with pollen from the recalcitrant maize plant; and (c) allowing progeny embryos to form. In successful crosses, the progeny plant is transformable. The recalcitrant maize plant may have a cytoplasm other than NA, for example, the cytoplasm other than NA is normal B ("NB") cytoplasm, cytoplasmic-male-sterile C ("C" or "CMS-C") cytoplasm, cytoplasmic-male-sterile S ("S" or "CMS-S") cytoplasm, or cytoplasmic-male-sterile T ("T" or "CMS-T") cytoplasm. The recipient maize plant may be a haploid inducer plant (or more specifically a paternal haploid inducer plant), or the paternal haploid inducer plant comprises a mutated ig1 gene or a CENH3 mutation.

Once produced, the progeny embryo is grown into a progeny plant. The progeny plant may be backcrossed with the recalcitrant maize plant for at least one generation. Alternatively, the progeny plant is the female parent in the backcross. The progeny plant may maintain the NA cytoplasm and/or maintains the nuclear genome of the recalcitrant maize plant.

A practitioner of the invention may backcross the progeny plant using the pollen from the recalcitrant plant for at least one crossing before transforming tissue derived from the progeny embryo. This would increase the proportion of recalcitrant nuclear DNA (see Table 1) but retain the new cytotype, such that any plant tissue derived from the BC1 generation or later possesses a higher transformation efficiency rate than the original recalcitrant plant.

Another embodiment of the invention is a method of transforming a plant by testing maize plant lines for markers indicative of NA cytoplasm and selecting at least one of those lines for transformation In one aspect, the test detects a G nucleotide at a position that corresponds to position 11 of mitochondrial DNA sequence SEQ ID NO: 7; or the test detects the presence of a sequence corresponding to SEQ ID NO: 7. Optionally, the test for markers indicative of NA cytoplasm further comprises forward primer SEQ ID NO: 5 and reverse primer SEQ ID NO: 6. Alternatively, the test for markers indicative of NA cytoplasm comprises probe SEQ ID NO: 7 and/or probe SEQ ID NO: 8, wherein the probes are differentially labeled with fluorophores.

BRIEF DESCRIPTION OF THE SEQUENCES IN THE SEQUENCE LISTING

SEQ ID NOs: 1-4 are marker sets for discriminating between CMS and normal cytoplasm. The forward and reverse primers (SEQ ID NOs: 1 and 2, respectively) amplify the initial target, and the CMS and normal cytoplasm probes (SEQ ID NOs: 3 and 4, respectively) labelled with different fluorophores that indicate which allele is detected.

SEQ ID NOs: 5-8 are marker sets for discriminating between Normal A and Normal B cytotypes. The forward and reverse primers (SEQ ID NOs: 5 and 6, respectively) amplify the initial target and the Normal A and Normal B probes (SEQ ID NOs: 7 and 8, respectively) labelled with different fluorophores that indicates which allele is detected.

Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject.

The term "cytotype" refers to the classification of the cytoplasm associated with a plant line. Presently known cytotypes include normal A ("NA") and normal B ("NB") cytoplasm, but also include the cytoplasmic male sterile cytotypes: cytoplasmic-male-sterile C ("C" or "CMS-C") cytoplasm, cytoplasmic-male-sterile S ("S" or "CMS-S") cytoplasm, and cytoplasmic-male-sterile T ("T" or "CMS-T") cytoplasm. The terms cytotype and cytoplasm are used interchangeably.

As used herein, "recalcitrant" refers to a plant line that is not transformable or essentially not transformable. In other words, its transformation efficiency is 0% or essentially 0%. The term recalcitrant is synonymous with "nontransformable," and these terms are used interchangeably.

"Transformable," "transformability," and the like, refers to a plant, a line of plants, or a plant cell (such as callus tissue or a protoplast) that is more readily accepting of foreign DNA and can stably integrate the foreign DNA into its genome.

The term "backcrossing" is understood within the scope of the invention to refer to a process in which a hybrid progeny is repeatedly crossed back to one of the parents.

The term "conditionally male sterile" means a phenotype of male sterility (i.e., an incapability to produce fertile pollen), which can be induced and/or repressed by certain conditions. In consequence, a plant can be "switched" from a male sterile to a male fertile phenotype by applying said certain conditions. Male sterility can be caused by various factors and can be expressed for example as a complete lack of male organs (anthers), degenerated pollen, infertile pollen etc. Based on the intensity of the condition the "switch" from male sterility to male fertility may be complete or incomplete. Most preferably, in the context of the present invention the term "conditionally male sterile" means a temperature-dependent male sterility and thereby means a nuclear male sterile phenotype, wherein the sterility is temperature de-pendent and can be reverted to fertility at a temperature of more than 35° C. (preferably between 35° C. and 43° C., more preferably between 37° C. and 40° C., most preferably at about 39° C.; preferably with an exposure for a preferred heat treatment time and a subsequent growing at ambient temperature).

The term "corresponding to" refers in the context of nucleic acid sequences means that when the nucleic acid sequences of certain sequences are aligned with each other, the nucleic acids that "correspond to" certain enumerated positions in the present invention are those that align with these positions in a reference sequence, but that are not necessarily in these exact numerical positions relative to a particular nucleic acid sequence of the invention. For example, in the alignment below, the T at position 13 of SEQ ID NO: 8 corresponds to the G at position 11 of SEQ ID NO: 7.

```
SEQ ID NO: 7  C G T A A A T T T T  G  T  T  T  G  A  T  G  C
Position      1 2 3 4 5 6 7 8 9 10 11 12 13 14 15 16 17 18 19

SEQ ID NO: 8  A T C G T A A A T T  T  T  T  T  T  T  G  A  T  G  C
Position      1 2 3 4 5 6 7 8 9 10 11 12 13 14 15 16 17 18 19 20 21
```

"Transformation efficiency" or "transformation rate" means a measure of the number of successfully transformed plants over the number of total attempts. This measure may be expressed quantitatively, e.g., as a percentage or a raw number, or qualitatively, e.g., "low" or "high."

The term "allele(s)" means any of one or more alternative forms of a gene, all of which alleles relate to at least one trait or characteristic. In a diploid cell, the two alleles of a given gene occupy corresponding loci on a pair of homologous chromosomes. In some instances (e.g., for QTLs) it is more accurate to refer to "haplotype" (i.e., an allele of a chromosomal segment) instead of "allele", however, in those instances, the term "allele" should be understood to comprise the term "haplotype". If two individuals possess the same allele at a particular locus, the alleles are termed "identical by descent" if the alleles were inherited from one common ancestor (i.e., the alleles are copies of the same parental allele). The alternative is that the alleles are "identical by state" (i.e., the alleles appear to be the same but are derived from two different copies of the allele). Identity by descent information is useful for linkage studies; both identity by descent and identity by state information can be used in association studies, although identity by descent information can be particularly useful.

The term "differentially labeled" indicates that two or more probes each possess a fluorophore distinct from the other, such that the presence or absence of each probe may be detected individually and regardless of whether the two or more probes are comprised within the same reaction.

The term "germplasm" refers to the totality of the genotypes of a population or another group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geo-graphical area, while the phrases "non-adapted germplasm", "raw germplasm", and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

The term "haplotype" can refer to the set of alleles an individual inherited from one parent. A diploid individual thus has two haplotypes. The term "haplotype" can be used in a more limited sense to refer to physically linked and/or unlinked genetic markers (e.g., sequence polymorphisms)

associated with a phenotypic trait. The phrase "haplotype block" (sometimes also referred to in the literature simply as a haplotype) refers to a group of two or more genetic markers that are physically linked on a single chromosome (or a portion thereof). Typically, each block has a few common haplotypes, and a subset of the genetic markers (i.e., a "haplo-type tag") can be chosen that uniquely identifies each of these haplotypes.

The terms "heterotic group" and "heterotic pool" are used interchangeably and refer to the relationship between breeding pools of maize populations. Broadly, the primary designations for heterotic pool are: Stiff Stalk ("SS," also called Iowa Stiff Stalk Synthetic, or "BSSS"), Non Stiff Stalk ("NSS"), and Iodent ("IDT"). See J. v. Hweerwaarden, et al., *Historical genomics of North American maize*, PROC. NAT'L ACAD. SCI. U.S.A. 109 (31):12420-25 (2012). These are not exclusive, however, and other designations are known, e.g., Lancaster Sure Crop ("LSC"). See, e.g., C. Livini, et al., *Genetic diversity of maize inbred lines with and among heterotic groups revealed by RFLPs*, THEOR. APPL. GENET. 84:17-25 (1992).

The terms "hybrid", "hybrid plant", and "hybrid progeny" in the context of plant breeding refer to a plant that is the offspring of genetically dissimilar parents produced by crossing plants of different lines or breeds or species, including but not limited to the cross between two inbred lines (e.g., a genetically heterozygous or mostly heterozygous individual). The phrase "single cross F1 hybrid" refers to an F1 hybrid produced from a cross between two inbred lines.

The phrase "inbred line" refers to a genetically homozygous or nearly homozygous population. An inbred line, for example, can be derived through several cycles of brother/sister breedings or of selfing. In some embodiments, inbred lines breed true for one or more phenotypic traits of interest. An "inbred", "inbred individual", or "inbred progeny" is an individual sampled from an inbred line. The term "inbred" means a substantially homozygous individual or line.

The terms "introgression", "introgressed" and "introgressing" refer to both a natural and artificial process whereby genomic regions of one species, variety or cultivar are moved into the genome of another species, variety or cultivar, by crossing those species. The process may optionally be completed by backcrossing to the recurrent parent.

The term "marker-based selection" is understood within the scope of the invention to refer to the use of genetic markers to detect one or more nucleic acids from the plant, where the nucleic acid is associated with a desired trait to identify plants that carry genes for desirable (or undesirable) traits, so that those plants can be used (or avoided) for any purpose, e.g., in a transformation program or in a selective breeding program. As used herein, a marker indicative of Normal A cytoplasm would discriminate between non-CMS plants having Normal B cytoplasm and those not having the Normal B cytoplasm, i.e., having the Normal A cytoplasm. A marker may be a mutation within a locus of a genome (e.g., a single nucleotide polymorphism ("SNP") or a mutation within one allele.

The phrase "phenotypic trait" refers to the appearance or other detectable characteristic of an individual, resulting from the interaction of its genome with the environment.

The term "plurality" refers to more than one entity. Thus, a "plurality of individuals" refers to at least two individuals. In some embodiments, the term plurality refers to more than half of the whole. For example, in some embodiments a "plurality of a population" refers to more than half the members of that population.

The term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the F1, the F2, or any subsequent generation.

The phrase "qualitative trait" refers to a phenotypic trait that is controlled by one or a few genes that exhibit major phenotypic effects. Because of this, qualitative traits are typically simply inherited. Examples in plants include, but are not limited to, flower color, cob color, and disease resistance such as for example Northern corn leaf blight resistance.

"Phenotype" is understood within the scope of the invention to refer to a distinguishable characteristic(s) of a genetically controlled trait.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any group of plant cells organized into structural and/or functional units. The use of this term in conjunction with, or in the absence of, any specific type of plant tissue as listed above or otherwise embraced by this definition is not intended to be exclusive of any other type of plant tissue.

The term "plant part" indicates a part of a plant, including single cells and cell tissues such as plant cells that are intact in plants, cell clumps and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as pollen, ovules, leaves, embryos, roots, root tips, anthers, flowers, fruits, stems, shoots, scions, rootstocks, seeds, protoplasts, calli, and the like.

The term "population" means a genetically heterogeneous collection of plants sharing a common genetic derivation.

The term "predominately male sterile" means that in a population of at least 100 plants not more than 10%, preferably not more than 5%, more preferably not more than 1% of the flowers on all of those plants have functional male organs producing fertile pollen. It has to be understood that an individual plant can have both fertile and sterile flowers. In preferred embodiments not more than 10%, preferably not more than 5%, more preferably not more than 1% of the flowers on an individual plant have functional male organs producing fertile pollen.

The term "offspring" plant refers to any plant resulting as progeny from a vegetative or sexual reproduction from one or more parent plants or descendants thereof. For instance, an offspring plant may be obtained by cloning or selfing of a parent plant or by crossing two parent plants and includes selfings as well as the F1 or F2 or still further generations. An F1 is a first-generation offspring produced from parents at least one of which is used for the first time as donor of a trait, while offsprings of second generation (F2) or subsequent generations (F3, F4, etc.) are specimens produced from selfings of F1's, F2's etc. An F1 may thus be a hybrid resulting from a cross between two true breeding parents (true-breeding is homo-zygous for a trait), while an F2 may be an offspring resulting from self-pollination of said F1 hybrids.

"Recombination" is the exchange of information between two homologous chromosomes during meiosis. The frequency of double recombination is the product of the frequencies of the single recombinants. For instance, a recombinant in a 10 cM area can be found with a frequency of 10%, and double recombinants are found with a frequency of 10%×10%=1% (1 centimorgan is defined as 1% recombinant progeny in a testcross).

The term "RHS" or "restored hybrid system" means a nuclear male sterility based hybrid system.

The phrases "sexually crossed" and "sexual reproduction" in the context of the present invention refer to the fusion of gametes to produce progeny (e.g., by fertilization, such as to produce seed by pollination in plants). In some embodiments, a "sexual cross" or "cross-fertilization" is fertilization of one individual by another (e.g., cross-pollination in plants). In some embodiments the term "selfing" refers to the production of seed by self-fertilization or self-pollination; i.e., pollen and ovule are from the same plant.

"Selective breeding" is understood within the scope of the present invention to refer to a program of breeding that uses plants that possess or display desirable traits as parents.

"Tester plant" is understood within the scope of the present invention to refer to a plant used to characterize genetically a trait in a plant to be tested. Typically, the plant to be tested is crossed with a "tester" plant and the segregation ratio of the trait in the progeny of the cross is scored.

The term "tester" refers to a line or individual with a standard genotype, known characteristics, and established performance. A "tester parent" is an individual from a tester line that is used as a parent in a sexual cross. Typically, the tester parent is unrelated to and genetically different from the individual to which it is crossed. A tester is typically used to generate F1 progeny when crossed to individuals or inbred lines for phenotypic evaluation.

The phrase "topcross combination" refers to the process of crossing a single tester line to multiple lines. The purpose of producing such crosses is to determine phenotypic performance of hybrid progeny; that is, to evaluate the ability of each of the multiple lines to produce desirable phenotypes in hybrid progeny derived from the line by the tester cross.

The terms "variety" or "cultivar" mean a group of similar plants that by structural or genetic features and/or performance can be distinguished from other varieties within the same species.

DETAILED DESCRIPTION

One embodiment of the invention is a method of increasing transformation efficiency rate in a recalcitrant maize line, comprising: (a) obtaining a recalcitrant maize plant and collecting pollen therefrom; (b) pollinating a recipient maize plant comprising normal A ("NA") cytoplasm with pollen from the recalcitrant maize plant; and (c) obtaining a progeny embryo therefrom; wherein the progeny embryo comprises the NA cytoplasm and at least the nuclear genome of the recalcitrant maize plant and wherein the progeny embryo possesses a higher transformation efficiency rate than the recalcitrant maize plant. Another embodiment is a method of conferring transformability to a recalcitrant maize line, comprising: (a) obtaining a recalcitrant maize plant and collecting pollen therefrom; (b) pollinating a recipient maize plant comprising normal A ("NA") cytoplasm with pollen from the recalcitrant maize plant; and (c) growing a progeny plant therefrom; wherein the progeny plant comprises the NA cytoplasm and the nuclear genome of the recalcitrant maize plant and wherein the progeny plant is transformable. In one aspect, the recalcitrant maize plant comprises a cytoplasm other than NA. In another, the cytoplasm other than NA is selected from the group consisting of normal B ("NB") cytoplasm, cytoplasmic-male-sterile C ("C" or "CMS-C") cytoplasm, cytoplasmic-male-sterile S ("S" or "CMS-S") cytoplasm, or cytoplasmic-male-sterile T ("T" or "CMS-T") cytoplasm. In one aspect, the recipient maize plant is a haploid inducer plant, or more specifically a paternal haploid inducer plant. In another aspect, the paternal haploid inducer plant comprises a mutated ig1 gene or a CENH3 mutation.

In another embodiment, the progeny embryo is grown into a progeny plant. In one aspect, the progeny plant is backcrossed with the recalcitrant maize plant for at least one generation. In another aspect, the progeny plant is the female parent in the backcross. In yet another, the progeny plant maintains the NA cytoplasm and/or maintains the nuclear genome of the recalcitrant maize plant.

In yet another embodiment, the invention is a method of increasing transformation efficiency rate in a recalcitrant plant line, comprising: (a) obtaining a recalcitrant plant and collecting pollen therefrom; (b) pollinating a recipient plant comprising transformable cytoplasm with pollen from the recalcitrant plant; (c) obtaining a progeny embryo therefrom; and (d) optionally (i) growing the progeny tissue into a progeny plant; (ii) backcrossing the progeny plant using the pollen from the recalcitrant plant for at least one crossing; and (e) transforming tissue derived from the progeny embryo; wherein the progeny tissue comprises the NA cytoplasm and at least the nuclear genome of the recalcitrant plant and wherein the progeny tissue possesses a higher transformation efficiency rate than the recalcitrant plant.

Another embodiment of the invention is a method of transforming a plant, comprising: (a) obtaining a plurality of plant lines; (b) testing for markers indicative of NA cytoplasm; (c) selecting at least one line from the plurality of plant lines wherein the selected lines possess markers for NA cytoplasm; and (d) transforming cells derived from the at least one selected line of step (c). In one aspect, the test detects a G nucleotide at a position that corresponds to position 11 of mitochondrial DNA sequence SEQ ID NO: 7. In another aspect, the test for markers indicative of NA cytoplasm detects the presence of a sequence corresponding to SEQ ID NO: 7. Optionally, the test for markers indicative of NA cytoplasm further comprises forward primer SEQ ID NO: 5 and reverse primer SEQ ID NO: 6. Alternatively, the test for markers indicative of NA cytoplasm comprises probe SEQ ID NO: 7 and/or probe SEQ ID NO: 8, wherein the probes are differentially labeled with fluorophores.

These and other embodiments of the invention will be more fully understood in light of the following non-limiting examples.

EXAMPLES

Example 1. Cytotype Transformability and Cytotype Transfer

Markers to distinguish between NA, NB, and CMS cytoplasms were developed based on the NA and NB mitochondrial genomes disclosed by James O. Allen, et al., *Comparisons Among Two Fertile and Three Male-Sterile Mitochondrial Genomes of Maize*, GENETICS 177:1173-1192 (October 2007), incorporated herein by reference. One hundred lines were cytoplasm genotyped with molecular markers that distinguish Normal from CMS cytoplasm (marker set 1; SEQ ID NOs: 1-4) and then with a NB marker only (marker set 2; SEQ ID NOs: 5-8). In this situation, the NA genotype is inferred when marker set 1 is affirmative (meaning the cytotype is not CMS) and marker set 2 is positive for the alternative allele (meaning the cytotype is other than NB). Eleven inferred NA lines were tested for transformation frequency using a standard transformation procedure, for example the procedure disclosed in US Patent Application Publication No. 2015/0113681, filed Oct. 23, 2013, incorporated herein by reference in its entirety. Line NP2222 is highly transformable and is used as a control to benchmark the transformation frequency.

TABLE 2

Transformation frequency of a selection of NA cytoplasm maize lines.

| Variety | Sum of Total # Events | Average of Transformation Freq. | Region | Heterotic Pool |
|---|---|---|---|---|
| Line 1 | 0 | 0 (n = 1) | Temperate | Stiff Stalk |
| Line 2 | 0 | 0 (n = 1) | Temperate | Stiff Stalk |
| Line 3 | 2 | 0.32 (n = 2) | Temperate | Stiff Stalk |
| Line 4 | 4 | 0.7 (n-2) | Temperate | Stiff Stalk |
| Line 5 | 2 | 0.8 (n = 1) | Temperate | Stiff Stalk |
| Line 6 | 13 | 1.3 (n = 4) | Temperate | Stiff Stalk |
| Line 7 | 25 | 4.3 (n = 2) | Temperate | Stiff Stalk |
| Line 8 | 25 | 6.25 (n = 1) | Temperate | Iodent |
| Line 9 | 62 | 6.8 (n = 3) | Temperate | Stiff Stalk |
| Line 10 | 610 | 50.1 (n = 3) | Temperate | Stiff Stalk |
| Line 11 | 455 | 51.7 (n = 3) | Temperate | Stiff Stalk |
| NP2222 | 315 | 31.8 (n = 5) | Temperate | Stiff Stalk |
| Line 17* | 0 | 0 (n = 1) | Temperate | Mixed |
| Line 18* | 34 | 6.8 (n = 2) | Sub-Tropical | Suwan |

*Lines 17 & 18 were tested in a second assay performed separately.

TABLE 3

NB lines and reciprocal crosses with NP2222.

| | Variety | Cytotype | Total Events | Average of Transformation Freq. |
|---|---|---|---|---|
| Crossing group 1 | Line 12 | NB | 0 | 0.0 |
| | Line 12 × NP2222 progeny | NB | 7 | 4.4 |
| | NP2222 × Line 12 progeny | NA | 9 | 4.1 |
| Crossing group 2 | Line 13 | NB | 0 | 0.0 |
| | Line 13 × NP2222 progeny | NB | 1 | 0.4 |
| | NP2222 × Line 13 progeny | NA | 3 | 0.8 |
| Crossing group 3 | Line 14 | NB | 9 | 4.5 |
| | Line 14 × NP2222 progeny | NB | 89 | 40.5 |
| | NP2222 × Line 14 progeny | NA | 92 | 46.0 |
| Crossing group 4 | Line 15 | NB | 0 | 0.0 |
| | Line 15 × NP2222 progeny | NB | 18 | 9.0 |
| | NP2222 × Line 15 progeny | NA | 23 | 10.3 |
| Crossing group 5 | Line 16 | NB | 0 | 0.0 |
| | Line 16 × NP2222 progeny | NB | 103 | 28.6 |
| | NP2222 × Line 16 progeny | NA | 71 | 22.5 |

In the crosses, the recipient line (i.e., female parent) is listed first and the pollen donor (i.e., male parent) is listed second. Without wishing to be bound by theory, it is believed that the NP2222 parent also imparts some other nuclear genetic factor that improves progeny transformability. Current transformation protocols are believed biased towards NP2222 and its derived lines. Even so, a 6% improvement (e.g., in crossing group 3) is a significant improvement in transformability, and a surprisingly good improvement at that.

By introducing the NA cytoplasm into the progeny, the transformation rate is significantly elevated in most lines compared to the recalcitrant parent having the NB cytotype. Even a modest increase in transformation rate, i.e., 0.0% to 0.8%, is a significant improvement over the nontransformability of the NB cytotype.

Example 2. Ig1-Mediated Cytotype Transfer

The maize mutant indeterminate gametophytel (ig1) produces maternal and paternal haploid progeny at 1-10% (Kindinger 1994). A NA transformable line was crossed by a heterozygous ig1 individual, PCR genotyped to identify heterozygous carriers and self-pollinated to create a NA version of the ig1 stock. F2 progeny were PCR genotyped and homozygous mutant ig1 individuals were pollinated by Line 13. One paternal haploid was identified and pollinated by the Line 13 recurrent parent. Transformation tests of the Normal B to Normal A were unsuccessful.

Example 3. No Detrimental Impacts on Yield

The effect of cytotype on hybrid yield was evaluated by reciprocally crossing Lines 7, 9, 10, 11 and NP2222 with Normal B testers and growing the progeny at approximately 10 yield trial locations. No obvious phenotypic differences were visible in the reciprocally crossed hybrid progeny and no statistically significant differences were observed across hybrids, locations or any of the interaction terms. This finding suggests that cytotype is an attribute that would not be expected to affect any obvious plant attribute and further exemplifies the significance of the differential effect on transformation competency.

Although the present invention has been described in considerable detail, other versions are possible. Therefore, the spirit and scope of the appended claims should not be limited to the description of the versions contained herein.

All features disclosed in this specification may be replaced by alternative features serving the same, equivalent, or similar purpose, unless expressly stated otherwise. Thus, unless expressly stated otherwise, each feature disclosed is one example only of a generic series of equivalent or similar features.

What is claimed is:

1. A method of increasing transformation efficiency rate in a recalcitrant maize plant, comprising:
   a. obtaining a recalcitrant maize plant and collecting pollen therefrom;
   b. pollinating a recipient maize plant comprising normal A ("NA") cytoplasm with pollen from the recalcitrant maize plant; and
   c. obtaining a progeny embryo therefrom;
   wherein the progeny embryo is grown into a progeny plant, and wherein the progeny plant comprises the NA cytoplasm of the recipient maize plant and at least the nuclear genome of the recalcitrant maize plant and wherein the progeny plant possesses a higher transformation efficiency rate than the recalcitrant maize plant, wherein the progeny plant comprising the NA cytoplasm of the recipient maize plant comprises the nucleic acid sequence of SEQ ID NO: 7.

2. The method of claim 1, wherein the recalcitrant maize plant comprises a cytoplasm other than NA.

3. The method of claim 2, wherein the cytoplasm other than NA is selected from the group consisting of normal B ("NB") cytoplasm, cytoplasmic-male-sterile C ("C" or "CMS-C") cytoplasm, cytoplasmic-male-sterile S ("S" or "CMS-S") cytoplasm, or cytoplasmic-male-sterile T ("T" or "CMS-T") cytoplasm.

4. The method of claim 1, wherein the recipient maize plant is a haploid inducer plant.

5. The method of claim 4, wherein the haploid inducer plant is a maternal haploid inducer plant.

6. The method of claim 5, wherein the maternal haploid inducer plant comprises a mutated ig1 gene or a Matrilineal gene.

7. The method of claim 4, wherein the haploid inducer plant is a paternal haploid inducer plant.

8. The method of claim 7, wherein the paternal haploid inducer plant comprises a CENH3 mutation.

9. The method of claim 1, wherein the progeny plant is backcrossed with the recalcitrant maize plant for at least one generation.

10. The method of claim 9, wherein the progeny plant is the female parent in the backcross.

11. The method of claim 9, wherein the progeny plant maintains the NA cytoplasm.

12. The method of claim 9, wherein the progeny plant maintains the nuclear genome of the recalcitrant maize plant.

13. A method of increasing transformation efficiency rate in a recalcitrant plant line, comprising:
   a. obtaining a recalcitrant plant and collecting pollen therefrom;
   b. pollinating a recipient plant comprising transformable cytoplasm with pollen from the recalcitrant plant;
   c. obtaining a progeny embryo therefrom; and
   d. optionally
      i. growing the progeny tissue into a progeny plant;
      ii. backcrossing the progeny plant using the pollen from the recalcitrant plant for at least one crossing; and
   e. transforming tissue from the progeny embryo;
   wherein the progeny tissue comprises the NA cytoplasm of the recipient maize plant and at least the nuclear genome of the recalcitrant plant and wherein the progeny tissue possesses a higher transformation efficiency rate than the recalcitrant plant, wherein the progeny embryo comprising the NA cytoplasm of the recipient maize plant comprises the nucleic acid sequence of SEQ ID NO: 7.

14. The method of claim 1, wherein the method further comprises detecting the progeny embryo comprising the NA cytoplasm by means of an assay comprising forward primer SEQ ID NO: 5 and reverse primer SEQ ID NO: 6, and probe SEQ ID NO: 7.

* * * * *